United States Patent
Weigel

(10) Patent No.: US 11,857,503 B2
(45) Date of Patent: Jan. 2, 2024

(54) CAPSULE CLOSURE DEVICE FOR CLOSING TWO-PIECE CAPSULES

(71) Applicant: Harro Hoefliger Verpackungsmaschinen GmbH, Allmersbach im Tal (DE)

(72) Inventor: Marco Weigel, Allmersbach im Tal (DE)

(73) Assignee: Harro Hoefliger Verpackungsmaschinen GmbH, Allmersbach im Tal (DE)

(*) Notice: Subject to any disclaimer, the term of this patent is extended or adjusted under 35 U.S.C. 154(b) by 475 days.

(21) Appl. No.: 16/523,672

(22) Filed: Jul. 26, 2019

(65) Prior Publication Data

US 2020/0046611 A1 Feb. 13, 2020

(30) Foreign Application Priority Data

Aug. 7, 2018 (EP) ..................................... 18187673

(51) Int. Cl.
*A61J 3/07* (2006.01)
*A61K 9/48* (2006.01)

(52) U.S. Cl.
CPC ............... *A61J 3/074* (2013.01); *A61J 3/072* (2013.01); *A61K 9/4833* (2013.01)

(58) Field of Classification Search
CPC . A61J 3/071; A61J 3/072; A61J 3/074; A61K 9/4833
See application file for complete search history.

(56) References Cited

U.S. PATENT DOCUMENTS

| 3,073,087 A * | 1/1963 | Ellsworth | ............... A61J 3/072 |
| | | | 53/485 |
| 3,552,095 A * | 1/1971 | Inman | ..................... A61J 3/075 |
| | | | 53/900 |

(Continued)

FOREIGN PATENT DOCUMENTS

| CN | 1761445 A | 4/2006 |
| DE | 20 2011 004 340 U1 | 6/2011 |

(Continued)

OTHER PUBLICATIONS

Office Action of the Indian Patent Office dated Nov. 16, 2022 in corresponding Indian patent application 201934029875.

(Continued)

*Primary Examiner* — Robert F Long
*Assistant Examiner* — Eduardo R Ferrero
(74) *Attorney, Agent, or Firm* — Walter Ottesen, P.A.

(57) ABSTRACT

A capsule closure device is for closing two-piece capsules each having a capsule upper portion and a capsule lower portion. The capsule closure device includes a capsule upper portion receiving member and a capsule lower portion receiving member. The capsule upper portion receiving member has a receiving hole and an introduction hole which is arranged coaxially relative to the receiving hole. The capsule upper portion receiving member has at the inner side thereof between the receiving hole and the introduction hole a support shoulder for supporting the capsule upper portion. The capsule upper portion receiving member has at the inner side thereof at the introduction hole at least one ventilation hole.

12 Claims, 2 Drawing Sheets

(56) References Cited

U.S. PATENT DOCUMENTS

| | | | | |
|---|---|---|---|---|
| 3,601,954 A * | 8/1971 | Aronson | A61J 3/074 | 53/122 |
| 3,978,640 A * | 9/1976 | Crossley | A61J 3/07 | 53/468 |
| 4,006,578 A * | 2/1977 | Gamberini | A61J 3/074 | 53/282 |
| 4,089,152 A * | 5/1978 | Zanasi | A61J 3/074 | 53/281 |
| 4,403,461 A * | 9/1983 | Goutard | A61J 3/072 | 53/282 |
| 4,415,387 A * | 11/1983 | Newman | B29C 66/112 | 156/69 |
| 4,539,060 A * | 9/1985 | Wittwer | B29C 65/4895 | 156/275.1 |
| 4,543,138 A * | 9/1985 | Bollinger | A61J 3/072 | 156/69 |
| 4,615,165 A | 10/1986 | Gamberini | | |
| 4,656,066 A * | 4/1987 | Wittwer | A61K 9/4883 | 428/34.1 |
| 4,677,812 A * | 7/1987 | Tayebi | A61J 3/072 | 156/294 |
| 4,724,019 A * | 2/1988 | Brown | A61J 3/072 | 156/69 |
| 4,731,979 A * | 3/1988 | Yamamoto | A61J 3/074 | 53/529 |
| 4,899,516 A * | 2/1990 | Krieger | A61J 3/072 | 118/317 |
| 4,964,262 A * | 10/1990 | Moser | A61J 3/074 | 53/506 |
| 4,991,377 A * | 2/1991 | Marchesini | A61J 3/072 | 156/69 |
| 5,018,335 A * | 5/1991 | Yamamoto | A61J 3/074 | 53/900 |
| 5,081,822 A * | 1/1992 | Boyd | A61J 3/074 | 53/281 |
| 5,111,642 A * | 5/1992 | Chiari | A61J 3/074 | 141/71 |
| 5,417,030 A * | 5/1995 | Ribani | A61J 3/074 | 53/281 |
| 5,515,740 A | 5/1996 | Gamberini | | |
| 6,170,226 B1 * | 1/2001 | Chang | A61J 3/074 | 53/253 |
| 6,327,835 B1 * | 12/2001 | Trebbi | A61J 3/074 | 53/53 |
| 6,367,228 B1 * | 4/2002 | Wurst | A61J 3/074 | 53/53 |
| 6,901,972 B1 * | 6/2005 | Nelson | A61J 3/074 | 141/247 |
| 7,082,738 B2 * | 8/2006 | Konishi | A61J 3/074 | 53/53 |
| 7,343,724 B1 * | 3/2008 | Williams | A61J 3/074 | 53/287 |
| 8,181,425 B2 * | 5/2012 | McCutcheon | A61J 3/072 | 53/329.2 |
| 8,596,025 B2 * | 12/2013 | Fulper | A61J 3/074 | 53/329 |
| 2003/0029558 A1 * | 2/2003 | Hochrainer | B29C 66/939 | 156/272.8 |
| 2005/0110192 A1 * | 5/2005 | Cade | A61J 3/072 | 264/275 |
| 2005/0217752 A1 * | 10/2005 | Facchini | A61J 3/074 | 141/146 |
| 2007/0184077 A1 * | 8/2007 | Vanquickenborne | A61J 3/072 | 424/400 |
| 2008/0141621 A1 | 6/2008 | Funaro et al. | | |
| 2008/0219803 A1 * | 9/2008 | Runft | A61J 3/074 | 414/21 |
| 2008/0236106 A1 | 10/2008 | Trebbi et al. | | |
| 2010/0009027 A1 | 1/2010 | Cade et al. | | |
| 2010/0212261 A1 * | 8/2010 | Boldis | A61J 3/072 | 53/403 |
| 2010/0281824 A1 * | 11/2010 | Ansaloni | A61J 3/074 | 53/266.1 |
| 2011/0088355 A1 | 4/2011 | Fulper | | |
| 2011/0247302 A1 | 10/2011 | Cade et al. | | |
| 2011/0277300 A1 * | 11/2011 | Hirota | A61J 3/074 | 29/428 |
| 2013/0014471 A1 * | 1/2013 | Tahil | A61J 3/072 | 53/284.5 |
| 2013/0186561 A1 * | 7/2013 | Van Rooyen | A61J 3/071 | 156/292 |
| 2015/0204714 A1 * | 7/2015 | Boehringer | G01G 17/00 | 53/281 |

FOREIGN PATENT DOCUMENTS

| | | |
|---|---|---|
| JP | 3419826 B2 | 6/2003 |
| WO | 2005084608 A1 | 9/2005 |

OTHER PUBLICATIONS

English translation and Chinese Office Action of the Chinese Patent Office dated Oct. 10, 2022 in corresponding Chinese patent application 201910725425.1.

* cited by examiner

CAPSULE CLOSURE DEVICE FOR CLOSING TWO-PIECE CAPSULES

CROSS REFERENCE TO RELATED APPLICATION

This application claims priority of European patent application no. 18 187 673.1, filed Aug. 7, 2018, the entire content of which is incorporated herein by reference.

BACKGROUND OF THE INVENTION

In particular in the pharmaceutical field, but also in the field of food supplements, or the like, easy-to-swallow capsules are used, the inner space of which is filled with active ingredient preparations or the like. Such capsules are constructed in two pieces and include a capsule lower portion and a capsule upper portion which is placed thereon. Widely used capsule materials are hard gelatin, HPMC (hydroxypropyl methylcellulose) or the like.

Empty capsules are supplied for filling in the loosely assembled state and supplied to a capsule closure device. This includes a capsule upper portion receiving member and a capsule lower portion receiving member, wherein the loosely assembled empty capsule first comes to rest in the capsule upper portion receiving member. From here, the capsule lower portion is removed from the capsule upper portion, for example, via reduced pressure, and introduced into the capsule lower portion receiving member. The filling of the capsule lower portion takes place in the capsule lower portion receiving member. Subsequently, the capsule lower portion is pressed, for example, via a stamp, relative to the capsule upper portion receiving member and introduced there into the capsule upper portion. During practical operation of such a capsule closure device, during the opening of the capsule high separation forces are required. Such separation forces are formed via a reduced pressure acting on the capsule lower portion. If the capsule lower portion has become released from the capsule upper portion, the capsule lower portion is conveyed by the high reduced pressure applied in such a rapid manner into the capsule lower portion receiving member that a so-called capsule jump can take place. The capsule jump occurs when the capsule lower portion strikes the capsule lower portion receiving member in an uncentered manner and a reverse pulse expels the capsule lower portion out of the capsule lower portion receiving member. Furthermore, with such high separation forces, the capsule base of the capsule lower portion can tear or break when striking the capsule lower portion receiving member. Since, when the capsule is closed, high forces are required, as a result of the stamp engaging on the base of the capsule lower portion, the base can be pressed in or even break.

SUMMARY OF THE INVENTION

It is an object of the invention to develop a capsule closure device in such a manner that the operational reliability thereof is increased.

This object can, for example, be achieved by a capsule closure device for closing two-piece capsules each having a capsule upper portion and a capsule lower portion. The capsule closure device includes: a capsule upper portion receiving member having an inner side; a capsule lower portion receiving member; the capsule upper portion receiving member defining a receiving hole and an introduction hole arranged coaxially relative to the receiving hole; the capsule upper portion receiving member having a support shoulder at the inner side between the receiving hole and the introduction hole; the support shoulder being configured to support the capsule upper portion; and, the capsule upper portion receiving member defining at least one ventilation hole at the inner side at the introduction hole.

The capsule closure device is based on the consideration that the required high forces for separating and closing the capsule are based on a lack of pressure compensation. When the capsule is separated, the capsule upper portion is supported along the capsule edge thereof on the support shoulder of the capsule upper portion receiving member. The capsule lower portion is in flush abutment with the introduction hole of the capsule upper portion receiving member. Consequently, the capsule upper portion and the capsule lower portion delimit an inner space whose volume expands with the downward movement of the capsule lower portion in the direction of the capsule lower portion receiving member. In this instance, the inner space remains at least initially substantially closed in an airtight manner. Accordingly, in the inner space between the capsule upper portion and capsule lower portion, there is formed a reduced pressure which makes separation of the capsule more difficult.

In order to reduce the high separation forces, the capsule upper portion receiving member has at the inner side thereof at the introduction hole at least one ventilation hole. Preferably, the capsule upper portion receiving member has at the inner side thereof at the introduction hole at least two, in particular three ventilation holes. Through the ventilation hole, when the capsule is opened, sufficient air can flow into the inner space between the capsule upper portion and capsule lower portion so that a pressure compensation is ensured. No or at most only a small reduced pressure is produced in the inner space. As the number of ventilation holes in the capsule upper portion receiving member increases, the pressure compensation can be carried out more rapidly. The capsule lower portion can be more readily separated from the capsule upper portion. As a result of the reduced separation forces, the capsule lower portion which is ultimately released is drawn into the capsule lower portion receiving member with less impact, whereby a capsule jump or other damage to the capsule can be prevented.

The pressure compensation is also carried out when the capsule is closed. When the capsule lower portion is pushed through the capsule upper portion receiving member into the capsule upper portion, the volume of the inner space between the capsule lower portion and the capsule upper portion is reduced. The excess air escapes through the ventilation hole, whereby excess pressure when the capsule is closed can be prevented. Accordingly, no excess pressure counteracts the closure force on the capsule lower portion. The forces can thereby be reduced when the capsule is closed so that any damage to the capsule as a result of excessively high closure forces can be prevented.

Preferably, the at least one ventilation hole extends from an outer side of the capsule upper portion receiving member to the inner side of the capsule upper portion receiving member and opens in the introduction hole of the capsule upper portion receiving member. When the capsule is opened, the air can thereby flow into the capsule upper portion receiving member or, when the capsule is closed, escape from the capsule upper portion receiving member. A pressure compensation with the environment is thereby ensured in the capsule upper portion receiving member in particular in the inner space between the capsule upper portion and the capsule lower portion.

The support shoulder of the capsule closure device typically has a peripheral inner edge. In such a case, the at least one ventilation hole advantageously forms an interruption of this inner edge. Accordingly, the ventilation hole opens precisely at the position in the capsule upper portion receiving member at which the capsule upper portion and the capsule lower portion overlap each other in the closed state. If the capsule lower portion is pulled out of the capsule upper portion, the pressure compensation in the inner space can already be carried out at the earliest possible time when the capsule lower portion and the capsule upper portion no longer overlap each other. When the capsule is closed, the pressure compensation can be carried out over the longest possible period of time until the capsule lower portion and capsule upper portion overlap each other again and delimit an air-tight closed inner space per se.

The capsule closure device preferably includes a suction device which is connected to the ventilation hole in order to extract dust particles in the capsule. The capsule can thereby be promptly cleaned of dust particles which, for example, have been deposited on the capsule during the filling operation with filling material or which have become disturbed during the closure operation.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
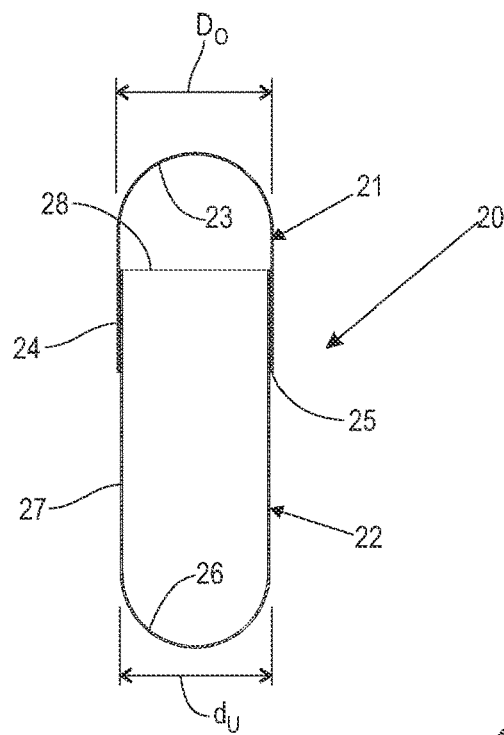
FIG. 1 is a schematic, partially sectioned side view of a two-piece capsule.

FIG. 1 is a schematic, partially sectioned illustration of a two-piece capsule 20, as used, for example, in the pharmaceutical sector or in the field of food supplements and which in the filled state contains an active ingredient preparation. In the ready filled and closed state, it is provided to be swallowed by a person. Various materials, such as hard gelatin, HPMC or the like, may be considered as the capsule material which dissolves after swallowing and releases the capsule contents.

The two-piece capsule 20 has a capsule upper portion 21 and a capsule lower portion 22, wherein the capsule lower portion 22 is inserted with a lower portion nominal diameter dU into the open side of the capsule upper portion 21 with a larger upper portion nominal diameter $D_O$. The capsule upper portion 21 includes as a conventional construction type a hemispherical cap portion 23 which a cylinder portion 24 adjoins. At the open side thereof, the capsule upper portion 21 is delimited by a peripheral capsule edge 25 of the cylinder portion 24. The capsule lower portion 22 is constructed in a similar manner to the capsule upper portion 21 and includes a hemispherical cap portion 26 which a cylinder portion 27 adjoins. At the side facing the capsule upper portion 21 and introduced at that location, the capsule lower portion 22 is delimited with a peripheral capsule edge 28 of the cylinder portion 27, wherein in the assembled state of the capsule upper portion 21 and capsule lower portion 22 a portion of the cylinder portion 27 together with the peripheral capsule edge 28 thereof comes to rest inside the cylinder portion 24 of the capsule upper portion 21.

Figure 2:
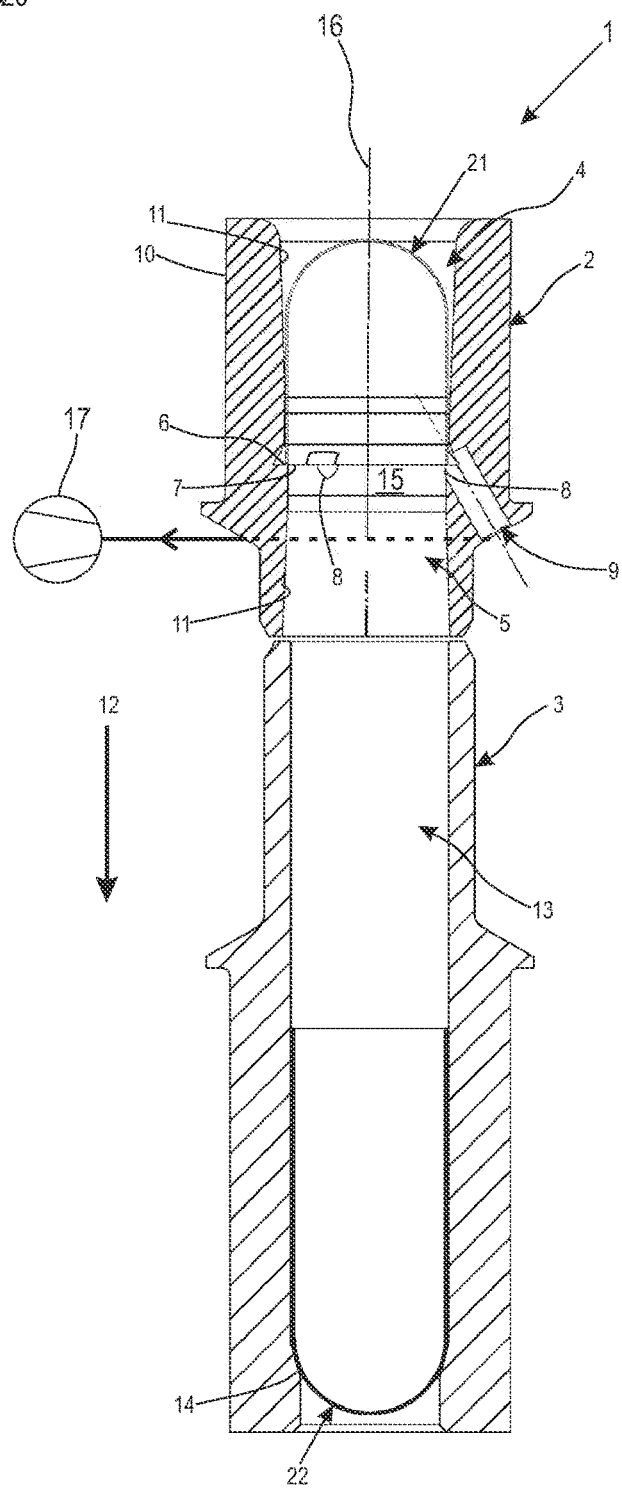
FIG. 2 is a longitudinally sectioned illustration of a capsule closure device according to the invention.

FIG. 2 is a longitudinally sectioned illustration of a capsule closure device 1 which includes a capsule upper portion receiving member 2 and a capsule lower portion receiving member 3. A capsule closure arrangement having a capsule upper portion 21 and a capsule lower portion 22 of a capsule 20 is arranged in the capsule closure device.

Empty capsules 20 according to FIG. 1 are delivered in a state in which the capsule lower portions 22 are loosely inserted into associated capsule upper portions 21 in each case. In this state, a single capsule 20 is introduced into the capsule closure device according to FIG. 2 from above in accordance with an arrow 12 in such a manner that they come to rest inside the capsule upper portion receiving member 2.

The capsule upper portion receiving member 2 has a receiving hole 4 for receiving the capsule upper portion 21 and merges in the direction toward the capsule lower portion receiving member 3 into a coaxially arranged introduction hole 5. The introduction hole 5 is reduced in terms of its diameter with respect to the diameter of the receiving hole 4 so that at the transition from the receiving hole 4 to the introduction hole 5 a peripheral support shoulder 6 is formed. The support shoulder 6 delimits the receiving hole 4 in a downward direction and is also in the same manner as the introduction hole 5 narrowed with respect to the receiving hole 4. The capsule 20 is introduced in accordance with the arrow 12 into the capsule upper portion receiving member 2 in such a manner that the capsule upper portion 21 comes to rest with the cylinder portion 24 thereof in the receiving hole 4, whilst the peripheral capsule edge 25 of the capsule upper portion 21 rests on the support shoulder 6. The support shoulder 6 has an inner diameter which is reduced with respect to the receiving hole 4 and through which the capsule lower portion 22 can be guided.

Below the capsule upper portion receiving member 2, the capsule lower portion receiving member 3 is positioned coaxially and includes a receiving hole 13. For example, via reduced pressure or the like, the capsule lower portion 22 which protrudes into the introduction hole 5 is pulled out of the capsule upper portion 21 into the receiving hole 13 of the capsule lower portion receiving member 3 in the direction of the arrow 12 until it comes to rest with the downwardly facing cap portion 26 thereof on a shoulder 14 which is reduced in terms of diameter with respect to the receiving hole 13. In this instance, the cylinder portion 27 of the capsule lower portion 22 is supported by the peripheral wall of the receiving hole 13.

The capsule lower portion 22 is filled with the active ingredient preparation which is not illustrated, while it is retained in the capsule lower portion receiving member 3. After completed filling, the capsule 20 is closed via the capsule closure device 1 by the capsule lower portion 21 being pressed, for example, via a stamp, which is not illustrated, counter to the direction of the arrow 12 upward through the receiving hole 13 and the introduction hole 5 into the capsule upper portion 21. In this instance, a counterforce is applied to the capsule upper portion 21 for spatial fixing thereof in the direction of the arrow 12, for example, via a stamp which is also not illustrated. During the closure operation, the peripheral capsule edge 28 of the capsule lower portion 22 slides radially at the inner side of the peripheral capsule edge 25 of the capsule upper portion 21 into the cylinder portion 24 thereof.

Figure 3:
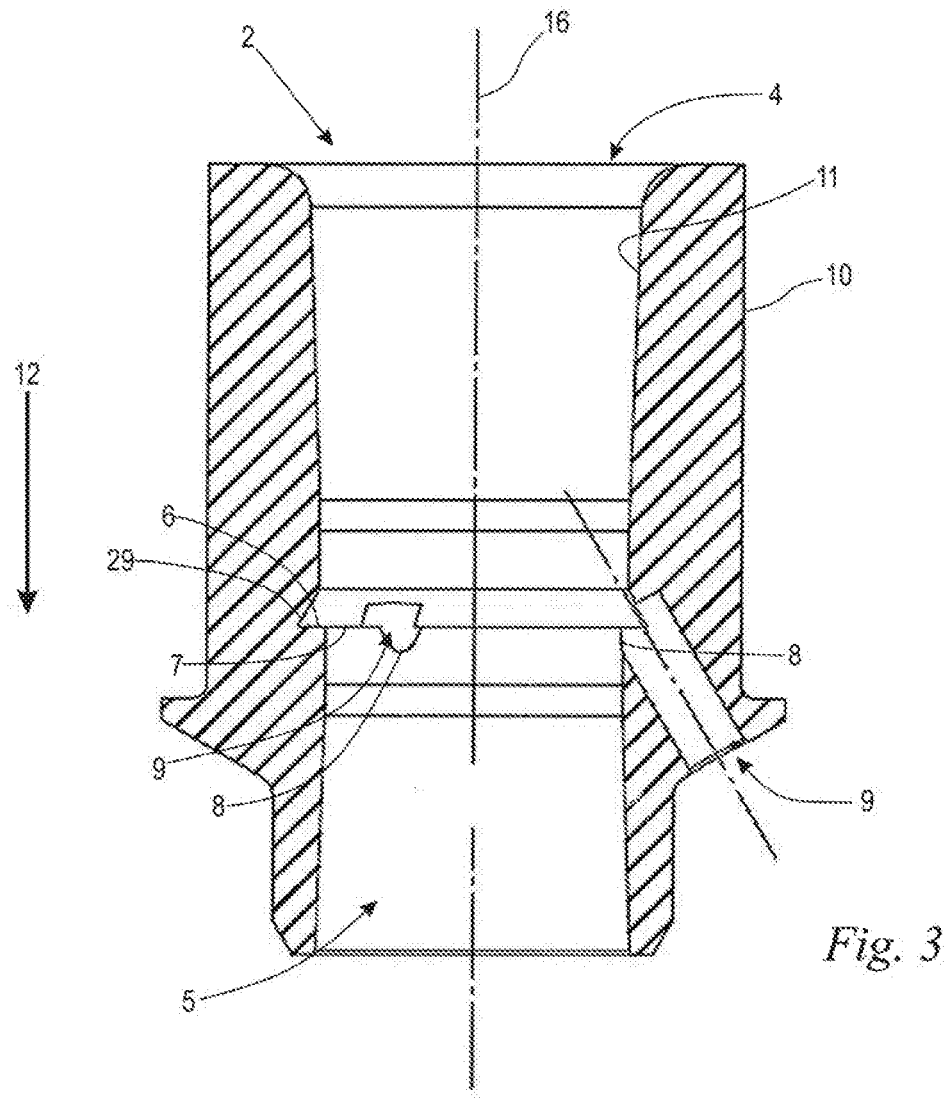
FIG. 3 is a sectioned illustration of the capsule upper portion receiving member; and, FIG. 4 is a perspective illustration of the capsule upper portion receiving member.

FIG. 3 is an enlarged sectioned illustration of the capsule upper portion receiving member 2 according to FIG. 2. The receiving hole 4 extends in the direction of the arrow 12 in a conical manner approximately up to the support shoulder 6. The receiving hole 4 is thereby constructed in a funnel-like manner and facilitates the introduction of the capsule 20 into the capsule upper portion receiving member 2. Directly adjacent to the support shoulder 6 there is formed a peripheral annular groove 29 which serves to receive filling material which has been discharged in an undesirable manner. The capsule edge 25 of the capsule upper portion 21 is thereby prevented from being pressed radially inward by the filling material which has accumulated on the support shoulder 6. The introduction hole 5 is constructed in a conical manner counter to the arrow direction 12. The introduction hole 5 tapers in a funnel-like manner in the direction of the support shoulder 6, whereby the introduction of the capsule lower portion 22 after the filling operation into the introduction hole 5 is promoted.

Figure 4:
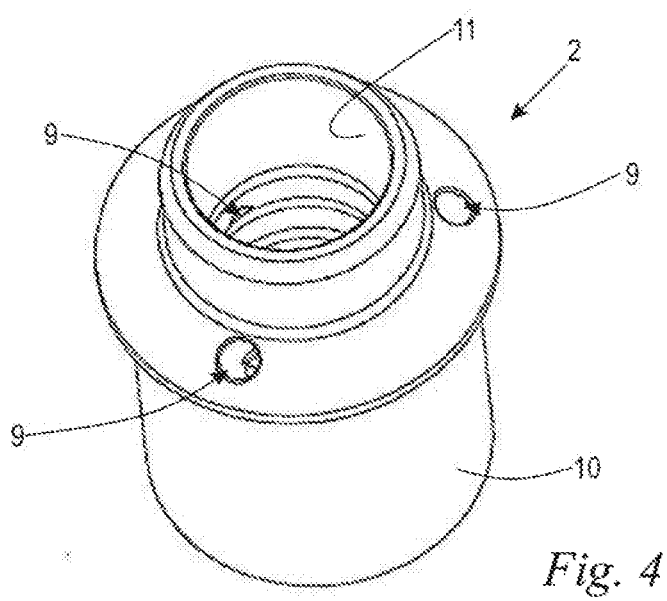

As shown in FIGS. 2 and 3, a plurality of ventilation holes 9 are formed in the capsule upper portion receiving member 2. The preferred embodiment of the capsule upper portion receiving member 2 has three ventilation holes 9 (FIG. 4). However, the construction of a single ventilation hole 9 may already be advantageous.

When the capsule 20 is separated, the capsule upper portion 21 is in abutment with the capsule edge 25 thereof flush with the inner side 11 of the receiving hole 4. If the capsule lower portion 22 is pulled out of the capsule upper portion 21, the capsule edge 28 of the capsule lower portion 22 is also in abutment flush with the inner side 11 of the introduction hole 5. In this instance, the capsule upper portion 21 and capsule lower portion 22 delimit an inner space 15. Through the ventilation hole 9, an air exchange between the inner space 15 and the environment outside the capsule upper portion receiving member 2 is enabled. Consequently, during separation and closure of the capsule 20, a pressure compensation takes place so that a reduced pressure or excess pressure which is applied in the inner space 15 can be prevented.

The ventilation hole 9 extends from an outer side 10 to the inner side 11 of the capsule upper portion receiving member 2 and opens in the introduction hole 5. In the embodiment, the ventilation hole 9 extends in an inclined manner with respect to the longitudinal axis 16 of the capsule upper portion receiving member 2, wherein another orientation of the ventilation hole 9 may be advantageous. In order to enable a pressure compensation, it may be sufficient to construct the ventilation hole 9 not as a through-hole, but only as a blind hole and thereby to provide an air reservoir for pressure compensation.

As shown in FIG. 3, in the preferred embodiment, the ventilation hole 9 extends through the support shoulder 6 and thereby forms an interruption 8 of the substantially peripheral inner edge 7 of the support shoulder 6. It may also be advantageous to construct the ventilation hole 9 adjacent to the inner edge 7 of the support shoulder 6, but at least adjoining, in a manner opening into the ventilation hole 9. The closer the ventilation hole 9 is located to the separation and closure point of the capsule 20, the earlier a pressure compensation can be carried out when the capsule 20 is separated and the longer the pressure compensation lasts when the capsule 20 is closed. The separation and closure point of the capsule 20 is located in the embodiment in the region of the support shoulder 6. With the interruption 8 of the inner edge 7 of the support shoulder 6, the capsule edge 25 of the capsule upper portion 21 does not abut the support shoulder 6 in an air-tight manner, whereby the earliest possible pressure compensation is ensured.

FIG. 4 is a perspective illustration of the capsule upper portion receiving member 2 according to the embodiment of FIG. 2. The three ventilation holes 9 are distributed in a peripheral direction of the longitudinal axis 16 of the capsule upper portion receiving member 2 with a uniform angular spacing of 120°. It may also be advantageous to construct the ventilation holes 9 in the capsule upper portion receiving member 2 with a non-uniform angular spacing in the peripheral direction of the longitudinal axis 16.

In an embodiment, the capsule closure device 1 may include a suction device 17 which is indicated only schematically in FIG. 2. The suction device 17 is connected to the one or the plurality of ventilation hole(s) 9 and serves primarily to extract dust particles which are adhering to the capsule 20. In order to clean the capsule 20, the suction device 17 is only switched on when the capsule 20 is already closed again after the filling operation. The capsule content is thereby prevented from being extracted by the suction device 17 from the capsule lower portion 3. In addition, the suction device 17 can also be used to clean the capsule upper portion receiving member 2 in terms of dust particles which are deposited, for example, on the inner side 11 of the capsule upper portion receiving member 2.

It is understood that the foregoing description is that of the preferred embodiments of the invention and that various changes and modifications may be made thereto without departing from the spirit and scope of the invention as defined in the appended claims.

What is claimed is:

1. A capsule closure device for separating and closing two-piece capsules each having a capsule upper portion and a capsule lower portion, wherein the capsule lower portion is pulled out of the upper capsule portion when separating an individual one of the capsules, and the capsule lower portion is inserted into the capsule upper portion when closing the individual one of the capsules, the capsule closure device comprising:

a capsule upper portion receiving member having an inner side and defining an inner space; and, a capsule lower portion receiving member;

said capsule upper portion receiving member defining a receiving hole and an introduction hole arranged coaxially relative to said receiving hole;

said capsule upper portion receiving member having a support shoulder at said inner side between said receiving hole and said introduction hole;

said support shoulder being configured to support the capsule upper portion;

said capsule upper portion receiving member defining at least one ventilation hole for a pressure compensation when pulling out and when inserting the capsule lower portion at said inner side at said introduction hole;

said at least one ventilation hole extending from an outer side of said capsule upper portion receiving member to said inner side of said capsule upper portion receiving member and opening in said introduction hole so as to provide the pressure compensation between said inner space of said capsule upper portion receiving member and an ambient outside of said capsule upper portion;

said support shoulder having a peripheral, radially inward inner edge;

said capsule upper portion receiving member defining a longitudinal axis;

said capsule upper portion receiving member having a smallest transverse section area on said inner edge of said support shoulder measured perpendicular to said longitudinal axis of said capsule upper portion receiving member; and, said at least one ventilation hole forming an interruption of said peripheral, radially inward inner edge.

2. The capsule closure device of claim 1, wherein said capsule upper portion receiving member defines at least two ventilation holes at said inner side at said introduction hole.

3. The capsule closure device of claim 1, wherein said capsule upper portion receiving member defines three ventilation holes at said inner side thereof at said introduction hole.

4. The capsule closure device of claim 1, wherein:
said capsule upper portion receiving member has an outer side; and,
said at least one ventilation hole extends from said outer side of said capsule upper portion receiving member to said inner side of said capsule upper portion receiving member and opens in said introduction hole.

5. The capsule closure device of claim 1 further comprising a suction device connected to said at least one ventilation hole in order to extract dust particles on the capsule.

6. The capsule closure device of claim 1, wherein said capsule upper portion receiving member has a smallest diameter at said inward inner edge of said support shoulder.

7. The capsule closure device of claim 1, wherein said capsule upper portion has a capsule edge formed thereon; said support shoulder defines a support surface whereon said capsule upper portion comes into contact with said capsule edge thereof.

8. The capsule closure device of claim 7, wherein said inner edge of said support shoulder is configured to delimit said support surface toward said longitudinal axis of said capsule upper portion receiving member.

9. The capsule closure device of claim 7, wherein said support surface lies in a plane perpendicular to said longitudinal axis of said capsule upper portion receiving member.

10. The capsule closure device of claim 7, wherein:
said introduction hole defines an inner side;
said at least one ventilation hole opens at said inner side of said introduction hole and at said support surface of said support shoulder in said inner space of said capsule upper portion receiving member; and,
said at least one ventilation hole interrupts said inward inner edge of said support surface of said support shoulder.

11. The capsule closure device of claim 1, wherein said ventilation hole is configured as a throughpass bore.

12. The capsule closure device of claim 1, wherein said ventilation hole defines a flow connection between said inner space of said capsule upper portion receiving member and the ambient external of said capsule upper portion receiving member.

* * * * *